US012558012B2

(12) United States Patent (10) Patent No.: US 12,558,012 B2
Ndaw et al. (45) Date of Patent: Feb. 24, 2026

(54) METHOD OF MONITORING A BIOMARKER WITH A URINE ANALYSIS DEVICE

(71) Applicant: Withings, Issy les Moulineaux (FR)

(72) Inventors: Inna Ndaw, Issy les Moulineaux (FR); Julius Dewavrin, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 342 days.

(21) Appl. No.: 18/521,596

(22) Filed: Nov. 28, 2023

(65) Prior Publication Data

US 2024/0188870 A1 Jun. 13, 2024

(30) Foreign Application Priority Data

Dec. 12, 2022 (EP) .................................... 22315324

(51) Int. Cl.
*A61B 5/20* (2006.01)
*A61B 5/00* (2006.01)
(52) U.S. Cl.
CPC ............ *A61B 5/207* (2013.01); *A61B 5/6891* (2013.01)
(58) Field of Classification Search
CPC ..... A61B 5/207; A61B 5/6891; A61B 10/007; G16H 10/40; G16H 40/40; G16H 40/63; G01N 33/493
See application file for complete search history.

(56) References Cited

U.S. PATENT DOCUMENTS

| | | | | |
|---|---|---|---|---|
| 9,867,513 | B1* | 1/2018 | Hall | ........................ A47K 13/24 |
| 2001/0031913 | A1* | 10/2001 | Ito | ........................ A61B 10/007 |
| | | | | 4/300 |
| 2019/0365307 | A1* | 12/2019 | Laing | ..................... G01D 21/00 |
| 2022/0202360 | A1 | 6/2022 | Aimon et al. | |

FOREIGN PATENT DOCUMENTS

| | | | |
|---|---|---|---|
| FR | | 3 126 611 A1 | 3/2023 |
| FR | | 3 126 612 A1 | 3/2023 |
| FR | | 3 126 613 A1 | 3/2023 |
| FR | | 3 126 614 A1 | 3/2023 |
| WO | WO 2020/172645 A1 | | 8/2020 |
| WO | WO 2021/175909 A2 | | 9/2021 |
| WO | WO 2021/175944 A1 | | 9/2021 |

OTHER PUBLICATIONS

European Search Report as issued in European Patent Application No. 22315324.8, dated Apr. 18, 2023.

* cited by examiner

*Primary Examiner* — Andrey Shostak
(74) *Attorney, Agent, or Firm* — Pillsbury Winthrop Shaw Pittman LLP

(57) ABSTRACT

A method of monitoring at least one biomarker with a measurement plan including a datum related to a predetermined biomarker to analyze and at least one temporal analyzing window to analyze the predetermined biomarker. At least one of collecting a urine sample and analyzing the urine sample is performed at least in response to determining that an internal time value is within the at least one temporal analyzing window of the measurement plan.

20 Claims, 11 Drawing Sheets

800

910 - opening a temporal testing window

914 - activating the urine presence sensor

916 - identifying the peeing user

918 - collecting a urine sample

919 - analysing a urine sample

910

922 - sending measurement data

924 - associating measurement data to user profile

926 - receiving confirmation request

928 - closing the temporal testing window

920

930 - modifying upcoming temporal testing windows

<u>800</u>

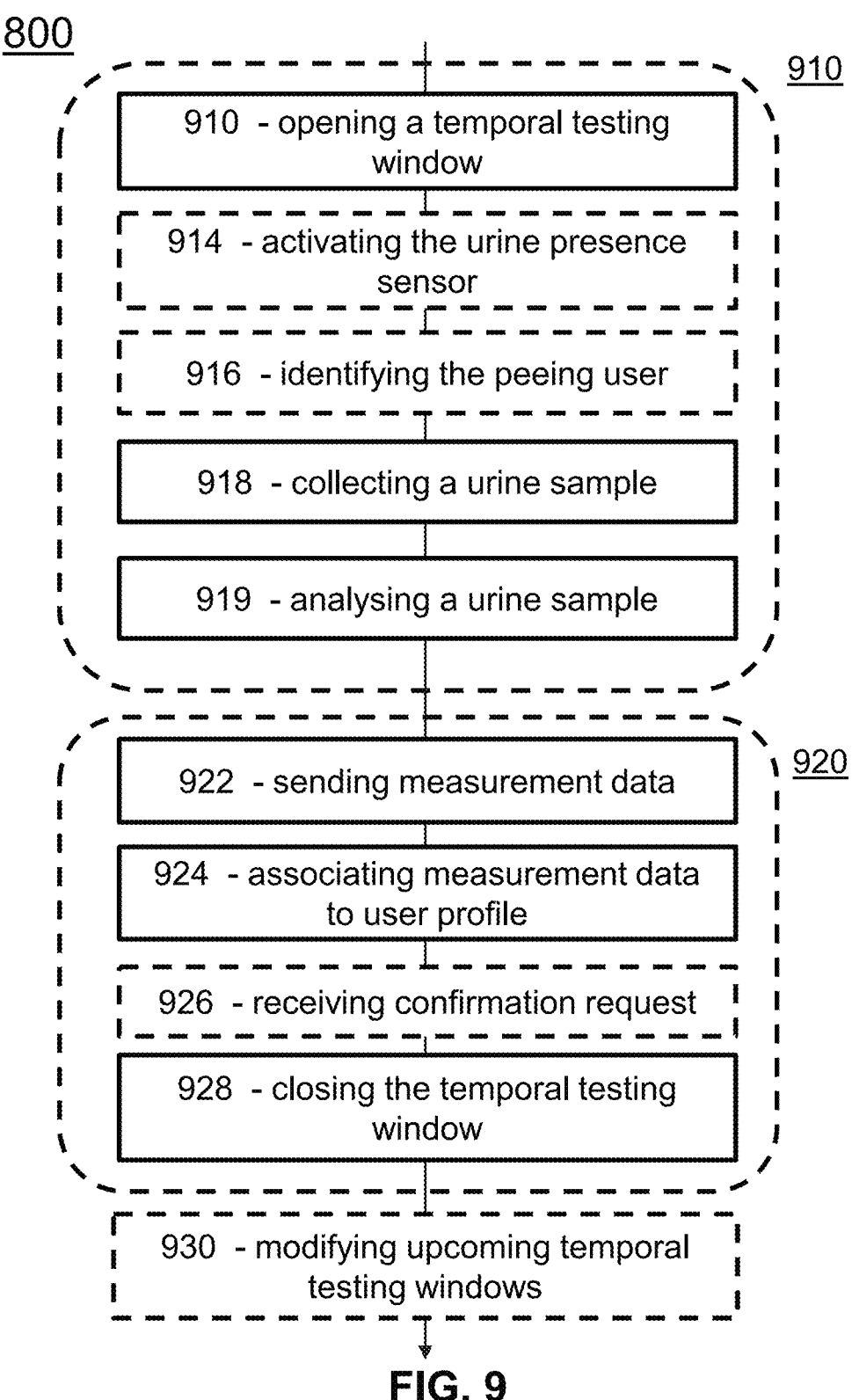

<u>910</u>

910 - opening a temporal testing window

914 - activating the urine presence sensor

916 - identifying the peeing user

918 - collecting a urine sample

919 - analysing a urine sample

<u>920</u>

922 - sending measurement data

924 - associating measurement data to user profile

926 - receiving confirmation request

928 - closing the temporal testing window

930 - modifying upcoming temporal testing windows

FIG. 9

METHOD OF MONITORING A BIOMARKER WITH A URINE ANALYSIS DEVICE

CROSS-REFERENCE TO RELATED APPLICATIONS

This application claims priority to European Patent Application No. EP22315324.8, filed Dec. 12, 2022, the entire content of which is incorporated herein by reference in its entirety.

FIELD

The present invention relates to a method of monitoring at least one biomarker with a urine analysis device. The urine analysis device may be installed on a surface of a toilet bowl.

BACKGROUND

Such a urine analysis device is notably described in document WO2021/175909. This document discloses a point-of-care device for urine analysis. The device is to be lodged in a toilet and collects a sample of a urine stream before performing an optical analysis. The device comprises a station and a cartridge, which is also called a rotatable support, and which may be removed and replaced from the station. The cartridge contains urinary test strips, that is to say strips coated or impregnated with a reagent that reacts with urine.

A user willing to carry out a urine analysis with such a device, and in particular willing to monitor a biomarker, launches an analysis request with a smartphone or a button remotely linked the device. Then, the user urinates on the urine analysis device which collects and analyses the urine to determine the selected biomarker.

However, if the user has to regularly monitor one or several biomarkers, the mental load is high for the user who must rely on his or her memory to remember to test his or her urine when needed. There is therefore a risk that users will forget or drop out of their biomarker monitoring process.

SUMMARY

An aspect of the description is to provide a method enabling an easy monitoring of at least one biomarker with no added mental load for the user.

To that end, the description relates to a method of monitoring at least one biomarker of a registered user with a urine analysis device in a toilet, the urine analysis device comprising control circuitry, the control circuitry comprising an internal clock and a memory storing at least one measurement plan associated to a user profile of the registered user, the at least one measurement plan comprising: a datum related to a predetermined biomarker to analyze and, at least one temporal analyzing window to analyze the predetermined biomarker. The method comprises:

collecting, by the urine analysis device, a urine sample from a urine stream of a urinating user, analyzing, by the urine analysis device, the urine sample to obtain measurement data relative to the predetermined biomarker of the urinating user, wherein at least one of collecting and analyzing is performed at least in response to determining that an internal time value of the internal clock is within the at least one temporal analyzing window of the measurement plan.

Thanks to this method, a personalized measurement plan is associated to the registered user, defining temporal analyzing windows when the user is expected to go to the toilets. This method enables an easy and regular monitoring without needing the user to remind to actively launch each urine analysis. The method according to an aspect of the invention allows the user to take the right test at the right time without further action aside from urinating normally. This is particularly beneficial for users wanting to monitor biomarkers that needs to be checked regularly, and which results depend on the regularity of the users (ovulation testing for example). Moreover, the method enables to avoid using test strips when not needed and may thus expand the lifetime of a cartridge.

For example, in the case of a daily monitoring, when a user has already monitored a biomarker in the morning, there is no use to analyze again his or her urine in the afternoon. Therefore, a temporal analyzing window is only defined in the morning, so that no analysis for this user and this biomarker is carried out in the afternoon.

As another example, the temporal analyzing windows enable to prevent other persons using the same toilets from having their urine analyzed. In a home with two people (e.g., a couple or roommates) who get up of bed at different moments, a temporal analyzing window around the expected awakening moment of a user avoids analyzing the urine of the other person if not needed.

In an implementation, the method further comprises: before collecting and/or analyzing, receiving and storing, by the urine analysis device, the at least an measurement plan in the memory.

In an implementation, the measurement data are associated to the user profile corresponding to the temporal analyzing window of the measurement plan.

In an implementation, the method further comprises: sending, by the urine analysis device, the measurement data to an external device.

In an implementation, the method further comprises, after sending: receiving, by an external device, a confirmation request including a request for input from the user to confirm that the measurement data is to be associated to his or her user profile.

In an implementation, the confirmation request comprises a transfer request to associate the measurement data to another selected registered user.

In an implementation, the memory stores a plurality of measurement plans, wherein at least two temporal analyzing windows of two measurement plans are at least partially overlapping.

In an implementation, the urine analysis device further comprises a urine presence sensor, wherein the collecting is performed in response to detecting, by the urine presence sensor, urine from a urine stream of the urinating user.

In an implementation, activating the urine presence sensor is performed at least in response to determining that an internal time value of the internal clock is within the at least one temporal analyzing window of the measurement plan.

In an implementation, the user selects on an external device a monitoring program among a plurality of predetermined monitoring programs, the monitoring program including at least a biomarker to measure and a measurement frequency associated to each biomarker, wherein the at least one measurement plan is generated using the monitoring program and the user profile.

In an implementation, the monitoring program comprises at least two biomarkers to analyze, a measurement plan being generated for each biomarker.

In an implementation, the user profile comprises awakening habits including at least one usual wakeup time for a given day, the at least one temporal analyzing window being generated using at least one usual wakeup time.

In an implementation, the at least one measurement plan is generated using further the associated biomarker to analyze.

In an implementation, the at least one temporal analyzing window including the at least one usual wakeup time.

In an implementation, the awakening habits are determined with data sent by a sleep monitoring device.

In an implementation, a sleep monitoring device detects that the user is getting out of his or her bed, a temporal analyzing window being created in response to the detecting.

In an implementation, in response to the user modifying his or her user profile using an external device, the at least one measurement plan is updated using the modified user profile.

In an implementation, the method further comprises: in response to the at least one measurement plan being updated, receiving, by the urine analysis device the at least one regenerated measurement plan once a day, in replacement of the at least one ongoing measurement plan.

In an implementation, the method further comprises: identifying, by the urine analysis device, at least a user profile associated with the urinating user.

In an implementation, at least one of collecting and analyzing the urine sample is performed in response to determining that one of at least one identified user profile is the user profile corresponding to the temporal analyzing window of the measurement plan.

In an implementation, the identifying includes determining at least a user characteristic associated to the urinating user, wherein at least one of collecting and analyzing the urine sample are carried out in response to further identifying the urinating user using the at least one user characteristic and the user profile corresponding to the temporal analyzing window of the measurement plan.

In an implementation, the user characteristic is the biological sex of the user.

In an implementation, the user characteristic is the identity of the user.

In an implementation, the at least one biomarker includes a Luteinizing hormone, wherein collecting and analyzing the urine sample are carried out only when the identified biological sex of the urinating user is a female.

In an implementation, the method further comprises calculating a confidence score related to the probability that the identified user profile is that of the urinating user, and in response to determining that the confidence score is lower than a predetermined threshold receiving, by an external device of the at least one identified user profile, a confirmation request for input to confirm that the identified user profile is to be associated to the urinating user.

In an implementation, the identifying is carried out with a radar sensor arranged in the urine analysis device, wherein the radar sensor sends a radar signal in direction of the urine stream and receives a reflected radar signal.

In an implementation, the method further comprises: calibrating the urine analysis device for the registered user, during which the radar sensor sends a radar signal in direction of a urine stream of a calibration urination of the registered user and receives a reflected radar signal, wherein the urine analysis device determines a user radar pattern associated to the user profile of the registered user based on the reflected radar signal, and wherein the identifying comprises comparing the received radar signal of the urinating user to the user radar pattern of the user profile.

In an implementation, the urine presence sensor is activated by the user with the user external device before calibrating.

In an implementation, the method comprises, after collecting the urine sample and before analyzing: identifying the user with the urine analysis device, wherein the identifying is based on a specific hormone in the urine sample.

In an implementation, the method comprises, after analyzing the urine sample: confirming the identification of the user with the urine analysis device, the confirmation step comprising detecting at least a specific hormone in the urine sample. This may be the measurement data or may be performed with a dedicated strip.

In an implementation, the urine analysis device determine that the user characteristic associated to the user biological sex of the urinating user is a female by detecting a concentration of Luteinizing hormone greater than a predetermined threshold in the urine sample.

In an implementation, the identifying is carried out with a weight sensor configured to obtain weight data of the user, the weight sensor sending a measure representative of the weight of a user sitting on the toilet bowl to the urine analysis device, the urine analysis device determining a user characteristic.

In an implementation, the method further comprises: receiving a reminder notification on a registered user external device before the beginning of a temporal analyzing window.

In an implementation, a temporal analyzing window is classified as unconclusive when no urine sample has been analyzed during the analyzing window, wherein when the number of analyzing windows classified as unconclusive over a predetermined period of time is greater than a predetermined threshold, the method further comprises: receiving, by an external device, a notification asking a user input to modify notably upcoming temporal analyzing windows of the measurement plan.

In an implementation, the upcoming temporal analyzing windows are refined (e.g., reduced) periodically based on the user habits.

In an implementation, the least one temporal analyzing window lasts longer on certain days of the week than on other days in the week.

In an implementation, the least one temporal analyzing window lasts longer during the weekend than on the rest of the week.

In an implementation, the method further comprises closing ongoing temporal analyzing window after measurement data is associated to the user profile associated with the ongoing temporal analyzing window.

According to another aspect, the description relates to a urine analysis device comprising control circuitry to perform any of the methods disclosed previously.

According to another aspect, the description relates to a system comprising a urine analysis device, a server and a mobile terminal, the system being configured to perform any of the methods disclosed previously.

According to another aspect, the description relates to a computer program comprising instructions which, when executed by a processor, such as a processor of a urine analysis device as disclosed previously, perform any of the methods disclosed previously.

BRIEF DESCRIPTION OF THE DRAWINGS

These features and benefits of an aspect of the invention will appear more clearly upon reading the following description, provided solely as a non-limiting example, and done in reference to the appended drawings, in which:

FIG. 9 illustrates a flowchart of monitoring at least one biomarker with a method according to the disclosure.

DETAILED DESCRIPTION

The present description will detail embodiments and variations of an automatic method of monitoring biomarker(s) using a urine analysis device. The present description will also detail embodiments and variations of a urine analysis device to perform those automatic method(s). However, unless specific otherwise, the method is not limited to the disclosed urine analysis device. For the sake of completion, one specific embodiment of such a urine analysis device will be given.

In that regard, the present description introduces different examples of urine analysis device including a station and a cartridge usable with the station as disclosed in document WO2021/175909 and WO2021/175944 (publication numbers), hereafter referred to as WO'909 and WO'944. Variations of the stations are presented in any of FR2109383, FR2109384, FR2109391, FR2109392 (filing numbers).

The next paragraphs explain the overall principal of a device for urine analysis, but all the details of WO'909 and WO'933 (and also any of the above-mentioned French filings) are applicable.

Overall Description of the Station and the Cartridge

Figure 1:
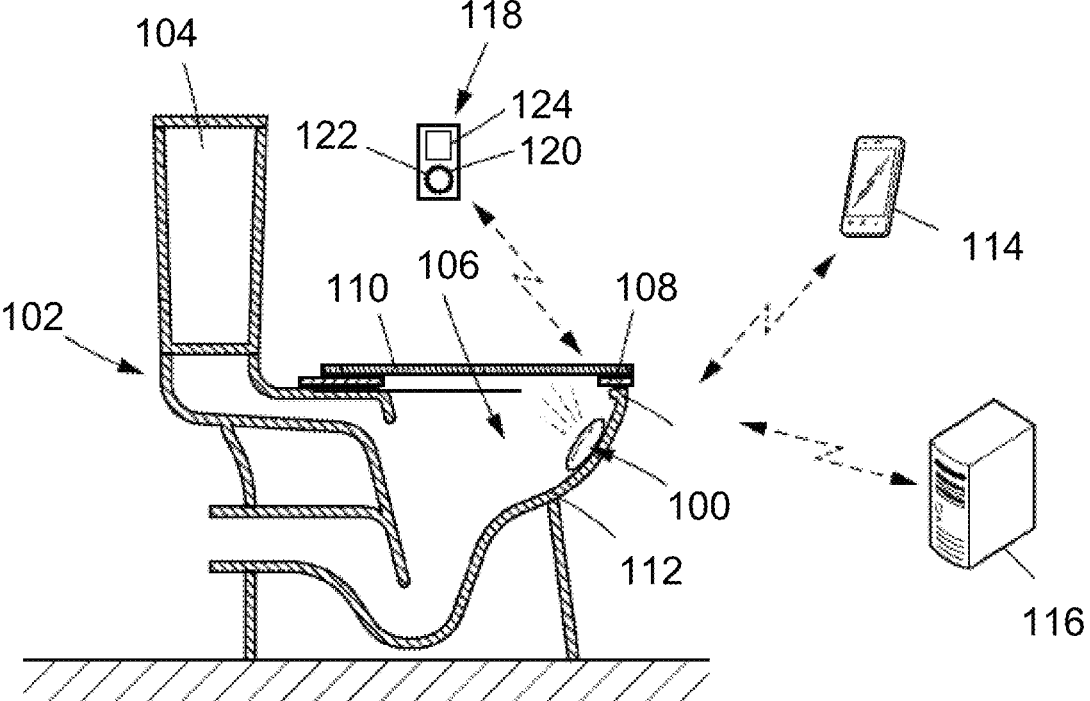
FIG. 1 shows the overall setup of a urine analysis device according to an embodiment, as installed on a surface of a toilet bowl.

FIG. 1 schematically illustrates an analysis device 100 (also referred to as the "device 100") for urine analysis as set up in toilets 102. Toilets 102 usually comprise a water tank 104, a bowl 106, a seat 108 and a seat cover 110. The analysis device 100 is arranged in a removable manner in the toilets 102. As illustrated, the analysis device 100 may be arranged in the toilet bowl 102. In a variant, the analysis device 100 may be arranged in the seat 108, in the seat cover 110, near the water tank 104, etc. For example, the analysis device 100 may be easily removed from the toilets to replace a cartridge and then arranged again in the toilets 102. The analysis device 100 is arranged on an internal wall 112 of the bowl 106 of the toilets. The analysis device 100 is placed so that it is usually under a urine stream from a user, such that when a user urinates (typically in a seated position), urine contacts with the analysis device 100. The analysis device 100 may communicate remotely with a remote entity, such as smartphone 114 or a server 116.

Figure 2:
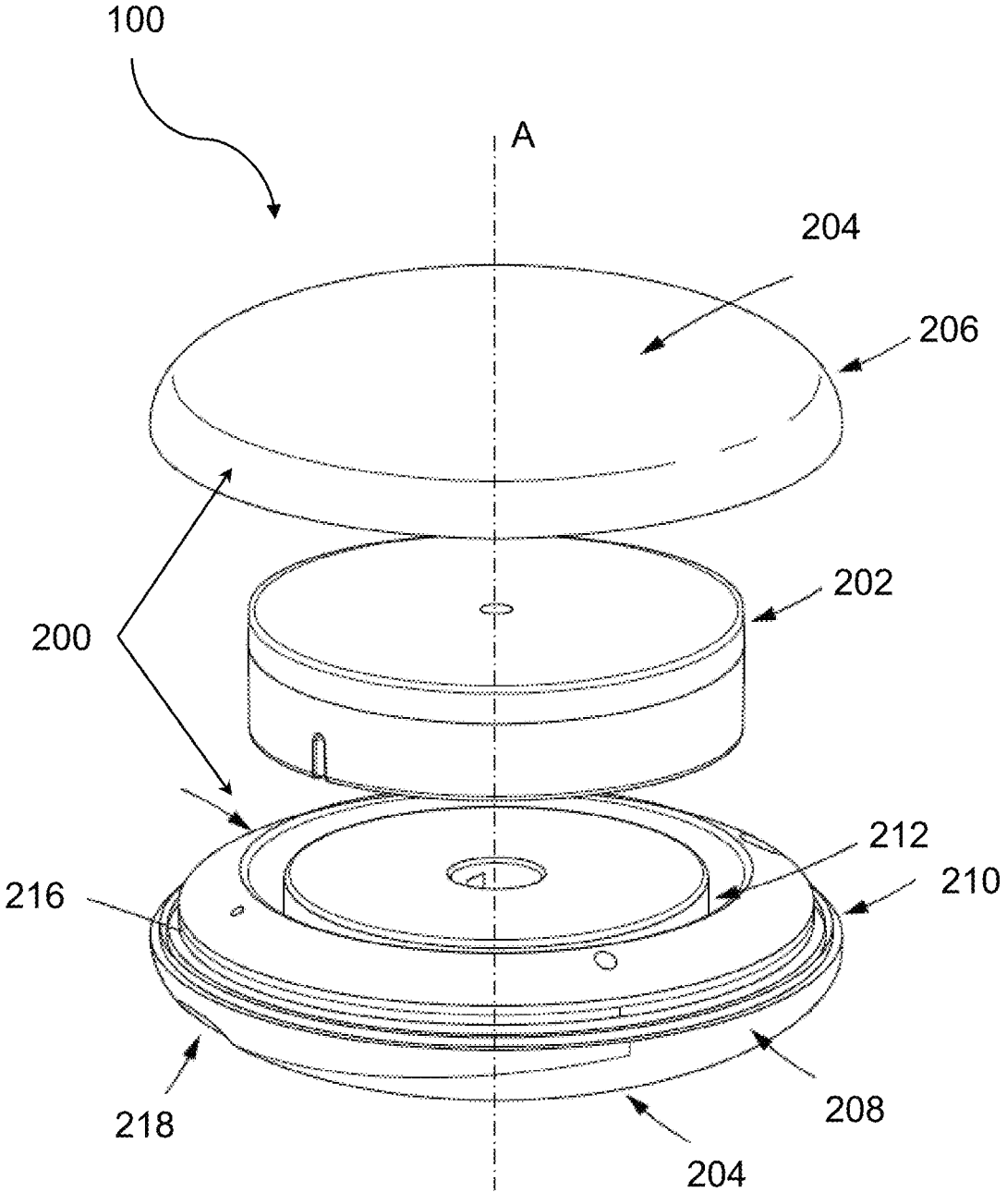
FIG. 2 shows an exploded view of the urine analysis device, in which the station and the cartridge are visible.

As illustrated in more detail on FIG. 2, the urine analysis device 100 comprises a station 200 and a cartridge 202, mounted in a removable manner from the station 200. Station 200 may comprise a housing 204 which may include two shells 206, 208. Case 204 lodges therein a urine testing assembly. Station 200 comprises an annular or ring-shaped housing 212, located inside the housing 204, arranged around a rotation axis A. The annular housing 212 is configured to receive at least partially the cartridge 202 mounted in a rotatable manner around the rotation axis A (once in position in the annular housing 212). The cartridge 202 comprises a plurality of test supports which each comprise at least one urine reagent to measure a biomarker, for instance a dry reagent, the plurality of test supports being arranged along a circle or a circular arc around the rotation axis A. In an embodiment, the test supports are test strips. The test supports may be enclosed, for example individually enclosed, in a chamber. The housing 204 may have a diameter, in a direction perpendicular to the rotation axis A, comprised between 50 mm and 150 mm.

The annular housing 212 typically extends around 360° and forms a groove configured to receive at least partially the cartridge 202.

Figure 3:
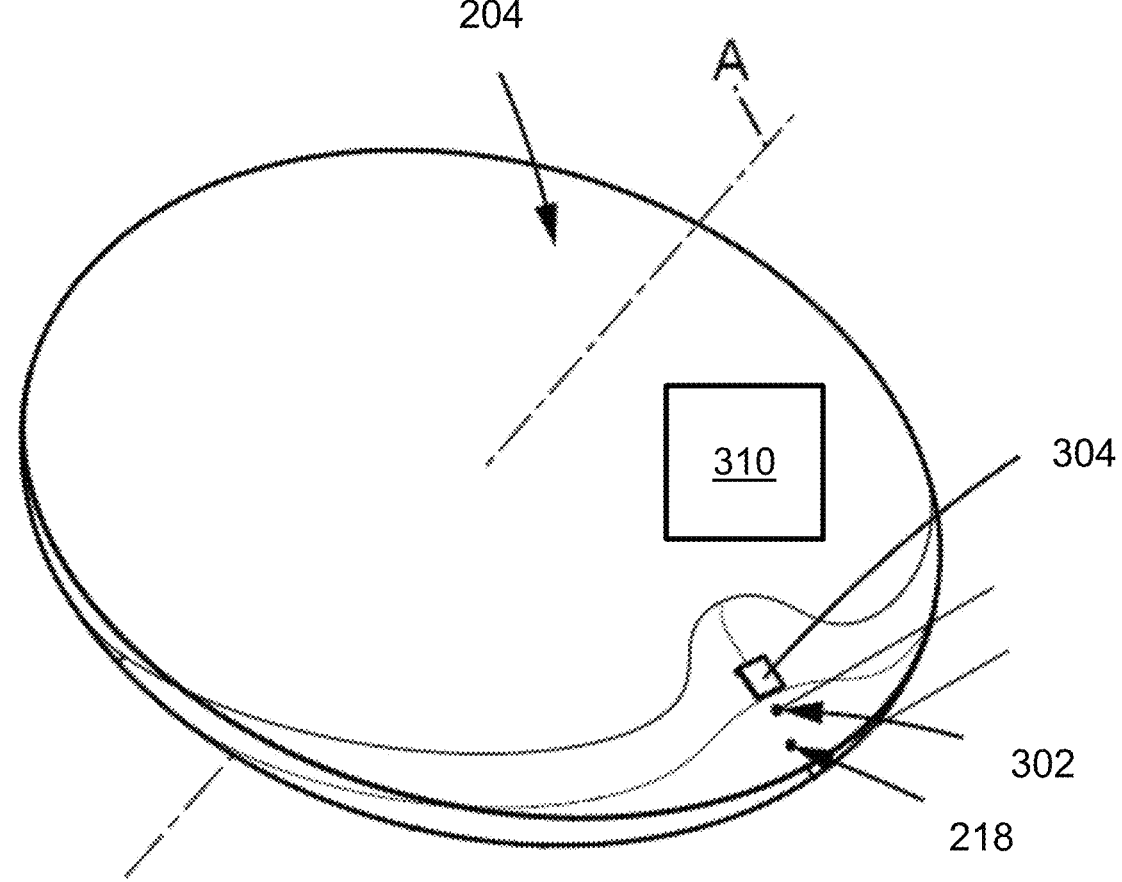
FIG. 3 shows a perspective view of the urine analysis device.

Referring to FIGS. 2 and 3, the station 200 comprises a collection opening 218, located for example on shell 208. The collection opening 218 collects urine flowing on the surface of the housing 204. A drain opening 302 is also included to drain the liquid out of the device 100. In particular, the collection opening 218 is configured to collect a urine sample from a urine stream of a urinating user.

Urine Presence Sensor

In an embodiment the urine analysis device 100 comprises a urine presence sensor 304, visible on FIG. 3.

The urine presence sensor 304 is arranged in the vicinity of the collection opening 218. The urine presence sensor 304 is configured to detect when urine is present in the vicinity of the collection port.

As it will be explained in detail below, the urine presence sensor 304 may be automatically activated or deactivated during predetermined periods of the day. The urine presence sensor 304 may further be activated by a user with an external device.

According to an embodiment, the urine presence sensor 304 may form a ring around the collection port. The integration of the urine presence sensor into the urine analysis device is then discrete.

The urine presence sensor 304 may be a temperature sensor, for example a thermistor. The temperature sensor is then configured to distinguish between urine and water from the toilet. In addition, the temperature sensor may also be operated to measure the temperature of the urine. The temperature of the urine may be used to detect periods of fertility, for example, by comparison with one or more reference curves.

Alternatively, the urine presence sensor 304 may be any type of liquid sensor, such as a capacitive or resistive type sensor. Then, a temperature sensor is separate from the urine presence sensor. The temperature sensor may be dedicated to measuring the temperature of the urine, in particular to detect a fertile period.

Alternatively, the urine presence sensor 304 may be a radar, a pressure sensor, a camera, a microphone or an infrared sensor.

Test Assembly

The test assembly comprises a pump, an injector and an analyzer.

The pump is configured to suck urine from the collection opening 218. In an embodiment, the pump is activated when a stream of urine is detected by the urine presence sensor 304.

The injector is configured to inject the urine on one or more test supports of the cartridge and an analyzer obtains some values of properties (e.g., physical/chemical properties, such as the color) of the test supports after it has contacted the urine. In an embodiment, the analyzer is an optical analyzer configured to analyze optical properties of the test support. The injector and the cartridge may move relative to each other so that the injector can open (e.g., pierce) the chamber, for example with a needle or needle-like device.

In particular, the analyzer is configured to analyze the urine sample to obtain measurement data relative to at least a biomarker of the urinating user. The measurement data may typically correspond to concentration of the biomarker in urine.

A biomarker, also called biological marker, is a characteristic that is objectively measured and evaluated as an indicator of normal biological processes, pathogenic processes or pharmacological responses to a therapeutic intervention. Biomarkers are here measured and evaluated using urine. Monitoring regularly such biomarkers enables for example to monitor wellness and nutrition markers. It may also enable to monitor women health, with cycle tracking, ovulation prediction, pregnancy determination, follow pregnancy, Perimenopause. It may also enable to monitor people with chronic disease, by detecting and monitoring of pathologies such as kidney disease or metabolic disorder. The analyzed biomarkers may be chosen among the following list: sodium, potassium, protein, creatinine, specific gravity, pH, ketones, glucose, vitamins, blood, leukocytes, nitrites, magnesium, chloride, urea, mercury, Luteinizing hormone (LH), human chorionic gonadotropin (hCG), etc.

Figure 4:
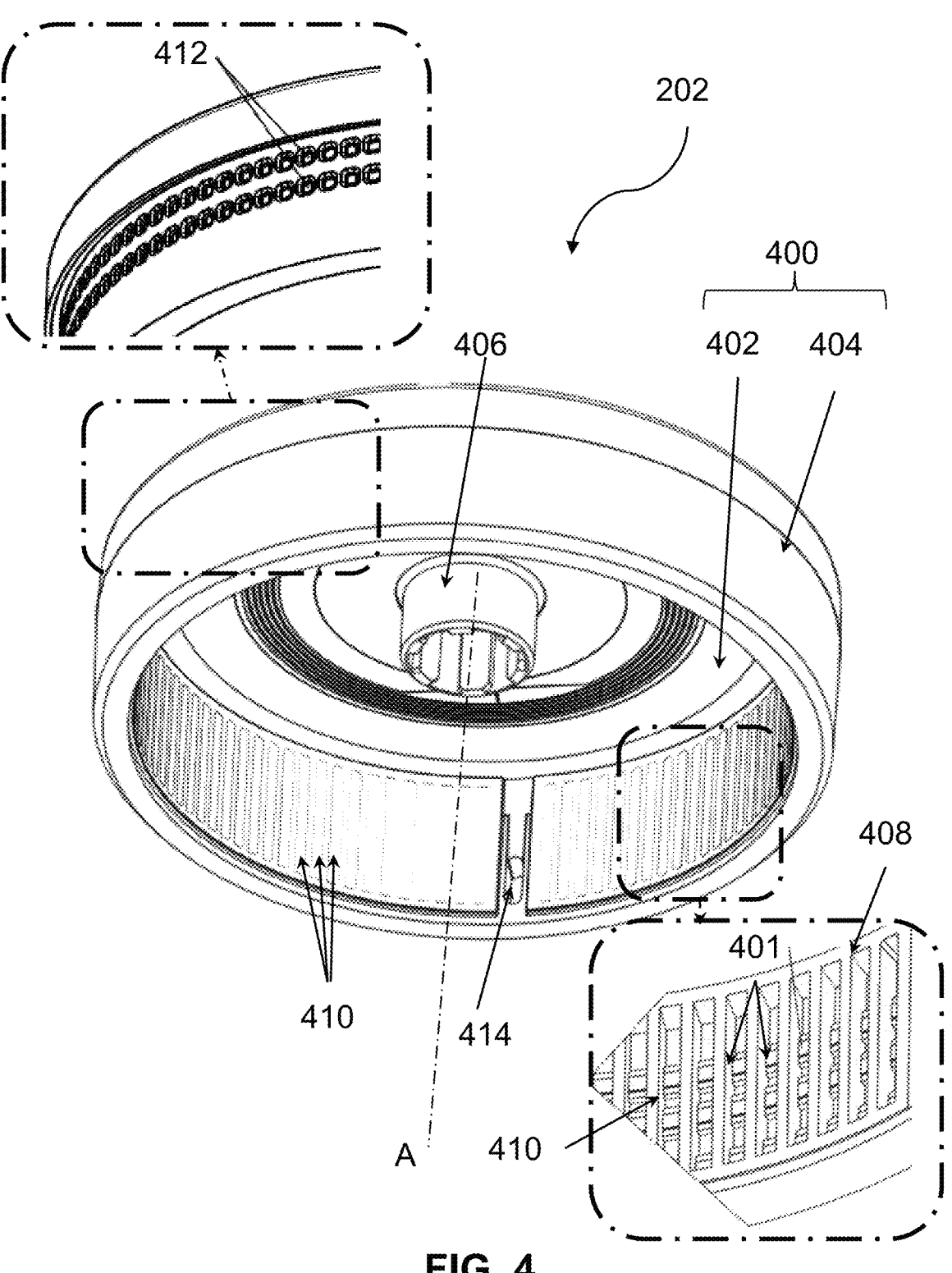
FIG. 4 shows a detailed view of a cartridge according to an embodiment.

FIG. 4 shows an exploded view of the cartridge 202. The cartridge 202 comprises test supports 401 configured to receive urine from the injector. The test support contains a urine reagent that reacts in a specific way when in contact with urine. The cartridge 202 comprises a rotatable support 400, configured to be driven in rotation by the station 200. In normal use of the cartridge 202 and the urine analysis device 100, the test supports 401 remain attached to the rotatable support and do not move with respect to the latter.

In an embodiment, the rotatable support 400 has a right circular cylinder shape of at least 80% of a circle a hollow cylinder shape extending annularly around an axis which is, when the cartridge 202 is mounted in the station 200, the rotation axis A. The test support 401 may be a test strip. The rotatable support 400 may comprise an annular portion 402 and a cylindrical portion 404, which extends from an outermost radial extremity of the annular portion 402. The cylindrical portion 404, when in use, is lodged inside the annular chamber 212. The test supports 401 are positioned along the cylindrical portion 404, so that they can be selectively and/or successively scrolled in front of the injector and the analyzer. For instance, the test supports 401 are part of a holder 408, which comprises several chambers 410, separated from each other along a perimeter around the axis A. The plurality of chambers 410 are arranged next to one another in a right circular cylinder shape of at least 80% of a circle. To allow light to go through, the holder 408 includes at least one aperture 412 per chamber 410 (represented in the upper left zoom where the rotatable support is shown as transparent). The chambers 410 are all at an equal distance of the rotation axis A, so that the injector can selectively inject urine after the desired chamber is positioned at a desired location facing the injector. The injector may translate towards the chamber 410 and pierce a lid closing the chamber 410 (visible on FIG. 5). A drain opening 414 is provided in the rotatable support 400 to allow evacuating urine from the injector to the outside of the device 100.

The annular portion 402 of the rotatable support 400 remains outside of the annular chamber 212 to strengthen the cylindrical portion and/or to drive in rotation the cartridge 202. To that end, the annular portion 402 may include a mechanical coupling 406, which cooperates with a shaft of the station 200.

The dimensions relative to the cartridge 202 are disclosed in WO'909, WO'933 and the above-mentioned French applications. The maximum dimension of the device 100 transversal to the rotational axis A is less than 15 cm, even less than 10 cm. The maximum dimension of the device along the rotation axis A is less than 5 cm.

Figure 5:
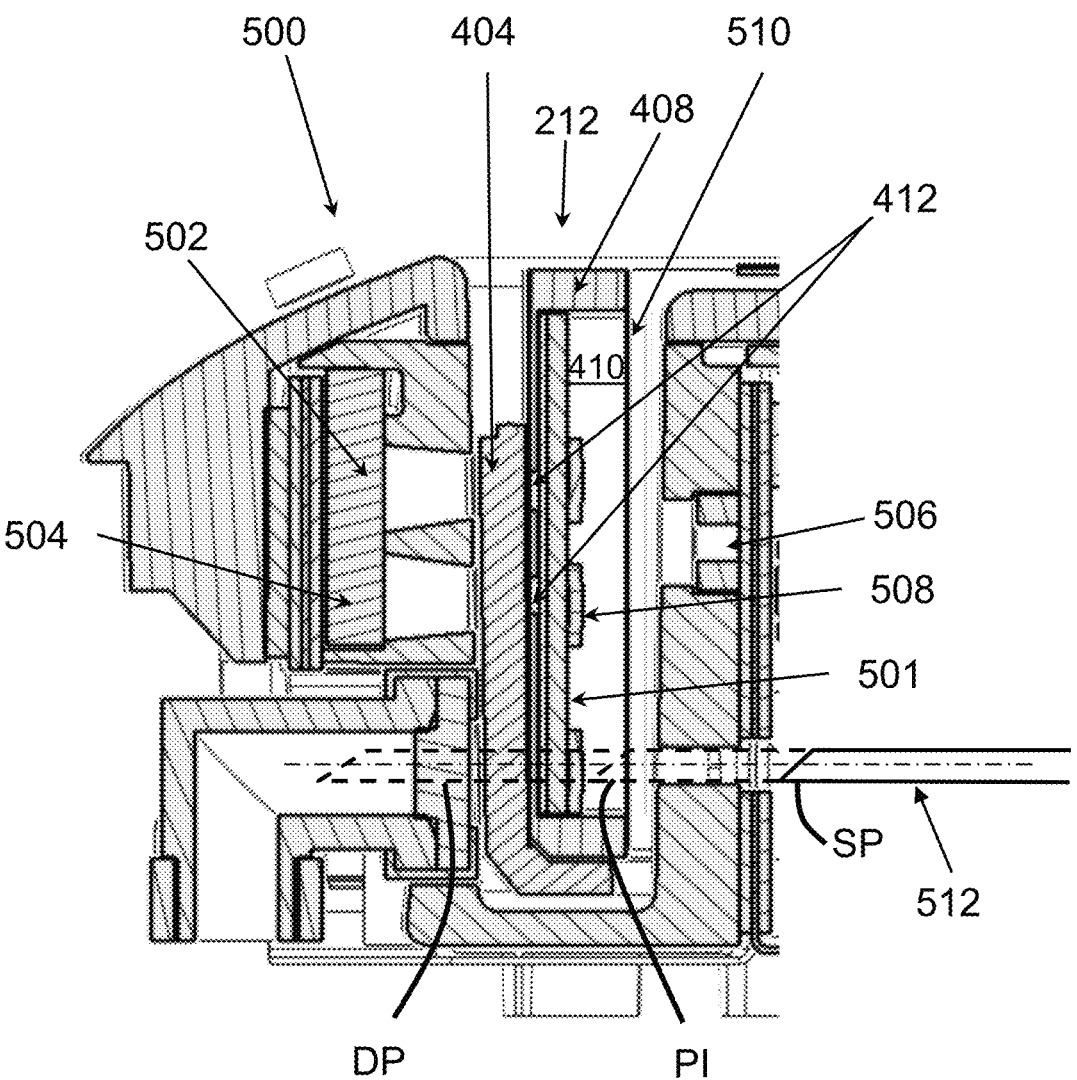
FIG. 5 shows a sectional view of an embodiment of a cartridge and a station, at the location of an optical analyzer of the station.

FIG. 5 shows in more detail the interaction between the cartridge 202 and the station 200 when or after the injector is activated. The analyzer 500 comprises at least one light source 502, 504 (e.g., two) and at least one optical sensor 506. Light travels from the light source 502, 504 to the optical sensor 506 while passing through the cartridge 202 and in particular the cylindrical portion 404, the aperture 412 of the holder 408, the test support 401 and thus the reagent 508. The injector includes an injection end 512 (for example a needle), which can be moved between several positions, which are represented in dash lines in FIG. 4. In a standby position SP, the injection end 512 is outside the cartridge 202 (in an innermost position), so that the cartridge 202 can rotate freely in the annular housing 212; in an injection position IP, the injection end 512 has pierced the lid 510 to access the inside of the chamber 310 and may inject some urine on the test support 401; in the drain position DP, the injection end 512 is able to evacuate urine through the drain opening 414 of the rotatable support 400.

In position SP, the injector is located radially inward the annular chamber. This allows to maximize the radius of the annular chamber while minimizing the size of the station 200.

Control Circuitry

Figure 6:
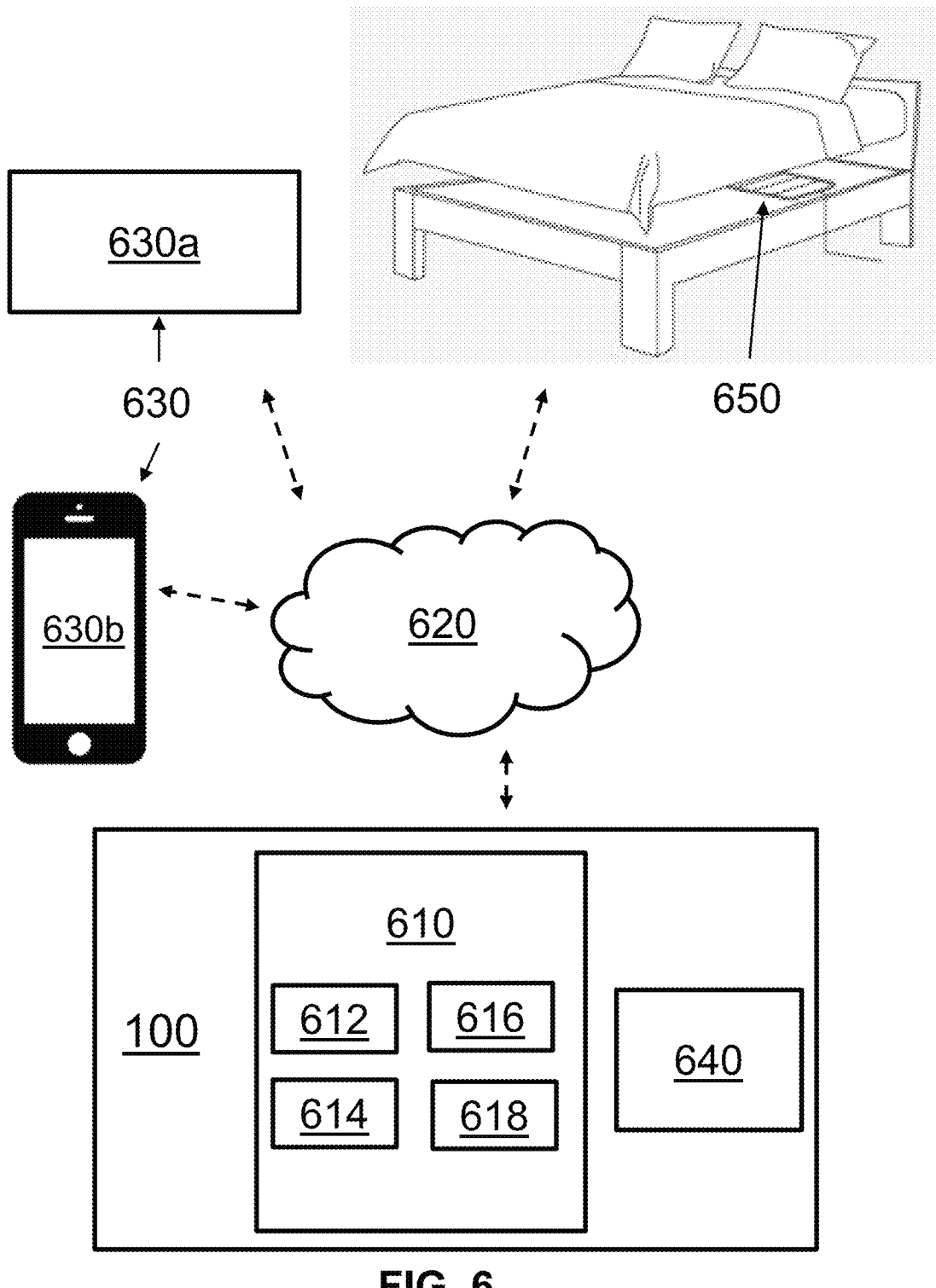
FIG. 6 shows a schematical view of the urine analysis device communicating with external devices.

In reference to FIG. 6, the urine analysis device 100 further comprises control circuitry 610 arranged inside the internal volume defined by the housing 204 with a processor 612, a memory 614, and an input/output (I/O) interface 616, which, among other things, allows the control circuitry 610 to receive and send data from and to a communication network 620. The processor 612 is configured to, among other things, process data obtained by sensors of the urine analysis device 100. The memory 614 may include machine readable instructions, which when they are executed by the processor 612, perform one or more of the functions of the urine analysis device 100, including, for example, the procedures of the methods described at FIGS. 8 and 9 described hereinafter. The control circuitry 610 further comprises an internal clock 618. The internal clock 618 may be part of the processor 612 or a separate circuit. The internal clock is for example an electronic circuit that produces a periodic, oscillating electronic signal, which is used to synchronize the operations of the control circuitry 610 and define an internal time. The control circuitry 610 and other electronic components may be mounted on a printed circuit board (PCB).

The urine analysis device 100, and in particular the input/output (I/O) interface 616, may communicate with at least an external device 630 via the communications network 620, which may include a wireless network (in particular a network compatible with at least one of the following communication protocols: BLUETOOTH® (a short-range wireless technology standard), Wi-Fi, cellular, etc.). The external devices 630 may include a server 630*a* and/or a mobile terminal 630*b* (smartphone, phablet, or even a webview on a computer, etc.). The device 100 may communicate with the server 630*a* and/or the mobile terminal 630*b*. In one implementation, the urine analysis device 100 may communicate directly with the mobile terminal 630*b*, for example via BLUETOOTH® or BLUETOOTH® Low Emission (BLE). This communication may be implemented at the installation of the urine analysis device 100, in particular to pair it with the mobile terminal 630*b* and/or to configure a connection to the server 630*a* that does not transit through the mobile terminal 630*b* and/or as a backup for a failed communication with the server 630*a*. In an embodiment, the urine analysis device 100 may communicate directly with the server 630*a*, without transiting through the mobile terminal 630*b*. This communication allows the user to use the weighing system 100 even without having the mobile terminal 630*b* nearby.

The mobile terminal 630*b* may run an application (also referred as an "app") with which the user may interact: data visualization, data input, device pairing, device settings, etc.

The urine analysis device 100 further comprises a battery 640 (e.g., rechargeable) arranged inside the internal volume configured for supplying power to the various components of the urine analysis device 100.

Other devices, such as a sleep monitoring device 650 may be connected to the external device 630 via the communications network 620. In an implementation, the sleep monitoring device 650 is provided underneath a support, e.g., a mattress, on which the user lies.

User Profile

A user profile is associated to at least one user of the urine analysis device 100. Each user associated to a user profile is called hereafter a registered user. Each user profile includes a plurality of user characteristics. The user characteristics may comprise a unique identifier (such as a user ID (identifier) number), the identity of the user (e.g., a name, nickname, or pseudonym), the biological sex of the user ("male", "female", etc.), the age of the user, the height of the user, the weight of the user, or any information characterizing the user, etc.). This is not limiting and it will be appreciated that others and/or additional user characteristics could be used in various embodiments. User characteristics may further include user lifestyle habits. The lifestyle habits comprise for example awakening habits including at least one usual wakeup time, e.g., usual wakeup time for a given day. The awakening habits may be determined with data sent by a sleep monitoring device 650 (e.g., as disclosed in US2022/202360). The lifestyle habits may further comprise home presence habits including for example remote working day, days off from work, holidays, etc.

The user profile is stored on at least an external device 630. The user profile is beneficially stored on the server 630*a* and at least a part of the user profile is stored on the user mobile terminal 630*b*. At least a part of the user profile is further stored in the control circuitry 610 of the urine analysis device 100. By "at least a part of the user profile", it is understood at least one of the user characteristics among all the user characteristics of the user profile. The server 630*a*, the mobile terminal 630*b* and the control circuitry 610 are configured to periodically communicate and exchange data, for example every day, to synchronize the user characteristic(s) which may have been modified on any of any of the server 630*a*, the mobile terminal 630*b* and the control circuitry 610. Synchronization can be carried out automatically or triggered by the user. For instance, a user may enter in the app (i.e. application) some data about himself or herself (manual logging), such that the user profile is updated in the app; upon synchronization the user profile on the server 630*a* and in the control circuitry 610 is also updated, either entirely or partially, for example updated with data only needed to perform any of the method presented in the description.

The user may modify his or her user profile, notably using the external device 630, by changing at least a user characteristic. As it will be further explained below, the user profile may comprise user lifestyle habits. In particular, the user profile may comprise awakening habits including at least one usual wakeup time for a given day.

The user may provide a lifestyle input about his or her lifestyle habits in the external device 630. In particular, the user may provide the lifestyle input in the mobile terminal 630*b* and the mobile terminal 630*b* is configured to send the information to server 630*a*. The server 630*a* is then configured to complete the user profile based on the input.

In variant or in complement, the lifestyle habits may be determined by a monitoring device located at the user home. For example, the awakening habits are determined with data sent by the sleep monitoring device 650. The sleep monitoring device may be a smart watch as for example a Withings ScanWatch or may be a device disposed in the user bed as for example a Withings Sleep. As another example, a home automation device may determine the house presence habits.

Identification System

In an embodiment, the urine analysis device 100 comprises an identification system 310, represented schematically on FIG. 3.

In particular, the identification system 310 is configured to identify at least one registered user associated with a urinating user, that is to say at least one user profile associated with the urinating user. To that end, the identification system 310 is configured to determine at least a user characteristic associated to the urinating user. The identification system 310 is configured to compare the determined user characteristic to the user characteristics of the user profiles stored in the memory 614 of the control circuitry 610. The identification system 310 is then configured to identify at least a user profile associated with the urinating user using the user profile(s) matching the determined urinating user characteristic.

The identification system 310 is configured to calculate a confidence score related to the probability that the identified user profile is that of the urinating user. In a variant, the confidence score may be calculated by the external device 630, notably the server 630*a*.

In an embodiment, the identification system 310 comprises a radar sensor arranged in the urine analysis device 100. The radar sensor is configured to send a radar signal in direction of the urine stream of the urinating user and to receive a reflected radar signal.

Due to the anatomical differences between a man and a woman, the position of the origin of the urine stream is not the same when the user is sitting on the toilets. In addition, the urine stream is different between a male and a female for various morphological reasons (urethral shape, pressure, flow rate, etc.).

The control circuitry 610 is then configured to process the received reflected radar signal and to determine at least one property related to the urine stream. These properties allow in particular to determine a user characteristic. The user characteristic is for example the biological sex of the user. The classification of a user can be at least a classification by discrimination between men and women. In an embodiment, the user characteristic may be the identity of the user, based on his or her particular morphological proprieties.

In an embodiment, the identification system 310 is calibrated for each registered user. Calibration enables to determine a user radar pattern for each registered user, enabling an effective identification with the identification system 310. In particular, during calibration, the radar sensor is configured to send a radar signal in direction of a urine stream of a calibration urination of the registered user and to receive a reflected radar signal. The identification system 310 is then configured to determine a user radar pattern associated to the user profile of the registered user based on the reflected radar signal. In an embodiment, several calibration sessions are performed for each user to generate a more precise user radar pattern. Thanks to this calibration, during the following urination session of the registered user, the radar sensors is configured to compare the received radar signal of the urinating user to the user radar pattern of the user profile so as to identify the urinating user.

Reference is made to French application FR2210069, which is incorporated by reference, for the details on the implementation of such a radar sensor.

In a variant or in complement, the identification system 310 is a hormone analyzer. The identification system 310 is then configured to identify the urinating user based on a specific hormone in a collected urine sample. For example, the identification system 310 is configured to determine that the user characteristic associated to the user biological sex of the urinating user is a female by detecting a concentration of Luteinizing hormone greater than a predetermined threshold in the urine sample.

In a variant or in complement, the identification system 310 is separated from the urine analysis device 100. The identification system 310 is then configured to communicate with the urine analysis device 100. The identification system 310 is notably a weight sensor arranged on the toilet bowl. The weight sensor is configured to obtain weight data of the user and to send a measure representative of the weight of a user sitting on the toilet bowl to the urine analysis device 100. The urine analysis device 100 is then configured to determine a user characteristic based on the measured weight. The user characteristic is for example a weight range associated to the user. Other examples of identification systems are presented in document WO2020/172645 for example.

Measurement Plan

The memory 614 of the control circuitry 610 stores at least one measurement plan associated to a user profile, referred to as the "associated user profile". As it will be explained in detail below, a measurement plan defines a schedule of measurements of a biomarker to be done by the user with the urine analysis device 100 during a period of time. The period of time may be predetermined (for example in case of post therapeutic intervention monitoring) or may be indefinite (for example in case of cycle tracking).

To that end, each measurement plan comprises a datum related to a predetermined biomarker to analyze, referred to as the "associated biomarker". A measurement plan is therefore associated to a single biomarker to analyze. The biomarker to analyze is associated to predetermined test supports 401 arranged in the cartridge 202.

In an embodiment, the memory 614 stores a plurality of measurement plans. The plurality of measurement plans may be associated to several users or to a single user but associated to several biomarkers. In that case, the cartridge 202 comprises a plurality of types of test supports 401, each type being associated to one biomarker to be analyzed.

Each measurement plan further comprises at least one temporal analyzing window to analyze the predetermined biomarker. A temporal analyzing window is a time period defined by a starting moment and an ending moment, or by a starting moment and a given duration. Each temporal analyzing window may last less than a day, for example less than 4 hours, for example less than 2 hours, for example less than 1 hour.

Therefore, a personalized measurement plan is associated to the registered user, defining temporal analyzing windows when the user is expected to go to the toilets. The measurement plan enables an easy and regular monitoring without needing the user to be reminded to actively launch each urine analysis or even to remember that he or she needs to have the urine analyzed. This is particularly beneficially for users wanting to monitor biomarkers that need to be checked regularly, and which results depend on the regularity of the users (ovulation testing for example). Moreover, the measurement plan enables to avoid using test strips when not needed and may thus expand the lifetime of a cartridge.

In an embodiment, each measurement plan is at least partially generated using user lifestyle habits, in particular awakening habits or home presence habits. The awakening habits includes at least one usual wakeup time for a given day and at least one temporal analyzing window is generated using at least one usual wakeup time. In particular, at least one temporal analyzing window includes the at least one usual wakeup time. In other words, a temporal analyzing window is generated around or right after the usual wakeup time of the user. This usual wakeup time often amount to an expecting urinating time, as waking-up is often quickly followed by urinating. The awakening habits may be determined with data sent by the sleep monitoring device 650.

In an embodiment, each measurement plan is generated using the associated biomarker to analyze. In particular, some biomarkers are better analyzed at some predetermined moment in the day. Some biomarkers, such as LH, are beneficially analyzed when the user is awakening and when the urine are more concentrated. Some biomarkers, such as pH, are beneficially analyzed at the end of the day.

In an embodiment, the external device 630 is configured to create a temporal analyzing window in response to detecting with a sleep monitoring device 650 that the user is getting out of his or her bed. In other words, the sleep monitoring device may detect that the user is getting out of bed, send an alert to the external device 630 (e.g., the server 630a) which in response automatically create a new temporal analyzing window. The new temporal analyzing window is then sent to the urine analysis device 100 via the communications network 620.

Some temporal analyzing windows may last longer on certain days of the week than on other days in the week. For example, temporal analyzing windows during a weekend may last longer than the rest of the week. Indeed, the lifestyle habits of a user are more uncertain during the weekend than the rest of the day, so that larger temporal analyzing windows reduce the risk for the user to miss them. Additionally or alternatively, the temporal analyzing windows of the weekend may be at a different time from that of the week: for example, the temporal analyzing window may be 7 am-8 am from Monday to Friday, and maybe 8 am-9 am on Saturday and Sunday.

In an embodiment, the external device 630 is configured to redefined periodically an upcoming temporal analyzing windows based on the user habits. In particular, the duration of the upcoming temporal analyzing windows may be reduced if the user urinates every day in an interval of time shorter than the temporal analyzing windows. For example, if a temporal analyzing window is active every morning between 8 am and 10 am but the user urinates every day around 9 am, the upcoming temporal analyzing windows may be reduced to 8:30 am until 9:30 am. On the contrary, the duration of the upcoming temporal analyzing windows may be increased and/or shifted in time if the user urinates every day near the starting point and/or the end point of the temporal analyzing windows. For example, if a temporal analyzing window is active every morning between 8 am and 10 am but the user urinates every day near 8 am or near 10 am, the upcoming temporal analyzing windows may be enlarged to 7:45 am until 10:15 am.

The different temporal analyzing windows of a same measurement plan are separated in time and are not overlapping: at any given time, there is only one temporal analyzing window of a measurement plan. The temporal analyzing windows may be periodic, for example daily, weekly, biweekly, monthly, etc.

In an embodiment, the memory 614 stores a plurality of measurement plans, wherein at least two temporal analyzing windows of two measurement plans may be at least partially overlapping. In particular, a user may be associated to several overlapping temporal analyzing windows of respective different measurement plan. For example, if the user follows two measurement plans, two temporal analyzing windows (one for each measurement plan) may be overlapping after his or her awakening. In complement or in variant, two users may be associated each to a temporal analyzing window, and those two temporal analyzing windows may turn out to overlap.

As it will be further described below, the predetermined biomarker of a user is only analyzed during each of the associated temporal analyzing window of the measurement plan. In other words, if the user urinates on the urine analysis device 100 outside (timewise) the temporal analyzing windows, the urine analysis device 100 does not measure the predetermined biomarker, and as a consequence does not use an associated test support 401.

To that end, when a user is urinating on the urine analysis device 100, the control circuitry 610 is configured to determine that an internal time value of the internal clock 618 of the urine analysis device 100 is within at least one temporal analyzing window of a stored measurement plan associated to this user, and, in response to such determination, is configured to instruct at least one of collecting and analyzing to be performed by the urine analysis device 100.

In particular, when the control circuitry 610 determines that the internal time value of the internal clock 618 is within only one temporal analyzing window associated to this user, the control circuitry 610 is configured to instruct collecting and analyzing to be performed by the urine analysis device 100 to measure the biomarker associated to the temporal analyzing window.

When the control circuitry 610 determines that the internal time value of the internal clock 618 is within at least two temporal analyzing windows associated to the same user, the control circuitry 610 is configured to instruct one collection of a urine sample and several analyses to be performed by the urine analysis device 100 to measure the at least two biomarkers associated to the temporal analyzing windows (one analysis per biomarker).

In an embodiment, the control circuitry 610 may be configured to activate the urine presence sensor in response to determining that an internal time value of the internal clock 618 is within the at least one temporal analyzing window of the measurement plan. The control circuitry 610 is configured to instruct one collection a urine sample when the urine presence sensor 304 detects a urine stream of the urinating user. As a consequence, outside the temporal analyzing windows, the urine presence sensor 304 is deactivated, and no urine collecting is performed. This enables saving the battery of the urine analysis device 100.

Identification Before Collecting/Analyzing

When the urine analysis device 100 comprises an identification system 310 as described above, the control circuitry 610 is configured to instruct at least one of a collection and an analysis the urine sample to be performed in response to determining that one of the at least one identified user profile is the user profile corresponding to the associated user profile of the measurement plan of the ongoing the temporal analyzing window. In other words, the urine analysis device 100 performs the collection and the analysis of a urine sample only when the urinating user is identified as being potentially the user of the user profile associated to the measurement plan of the ongoing temporal analyzing window. This avoids analyzing the biomarker of another user.

When the identification system 310 identifies a single user profile corresponding to the urinating user, the control circuitry 610 is configured to instruct at least one of collecting and analyzing the urine sample to be performed in response to determining that the identified user profile is the associated user profile of the measurement plan of the ongoing temporal analyzing window.

In particular, the control circuitry 610 is configured to instruct at least one of collecting and analyzing the urine sample in response to identifying the urinating user using at least one user characteristic (e.g., the biological sex) and the user profile corresponding measurement plan of the ongoing temporal analyzing window. In other words, the identification system 310 enables to discriminate the urinating user by determining at least a user characteristic, such as the biological sex of the user. For example, if a user characteristic of the user profile associated to the ongoing temporal analyzing window is "woman" (biological sex of the user), the identification system 310 may identify the biological sex of the urinating user and the control circuitry 610 launches collecting and/or analyzing only upon determining that the urinating user is a woman.

In an embodiment, the control circuitry 610 is configured to send to the external device 630, notably the mobile terminal 630*b*, a confirmation request. The confirmation request asks the user associated to the ongoing temporal analyzing window for an input to confirm that the identified user profile is to be associated to the urinating user. Such a request may be sent in response to a determination that the confidence score is lower than a predetermined threshold. For example, if the confidence score is lower than 75%, a confirmation request is sent to the user associated to the ongoing temporal analyzing window to confirm that he or she is the urinating user. In a variant, the confirmation request may be sent by the server 630*a*. For example, the confirmation request may by a pop-up in the app on the mobile terminal 630*b*.

Connectivity

In an embodiment, the urine analysis device 100 is configured to receive and store the at least one measurement plan in the memory 614. The measurement plan may be determined using inputs from the user on the mobile terminal 630*b*. In particular, the user may select on the external device 630, for example in an app in the mobile terminal 630*b*, a monitoring program among a plurality of predetermined monitoring programs.

Figure 7:
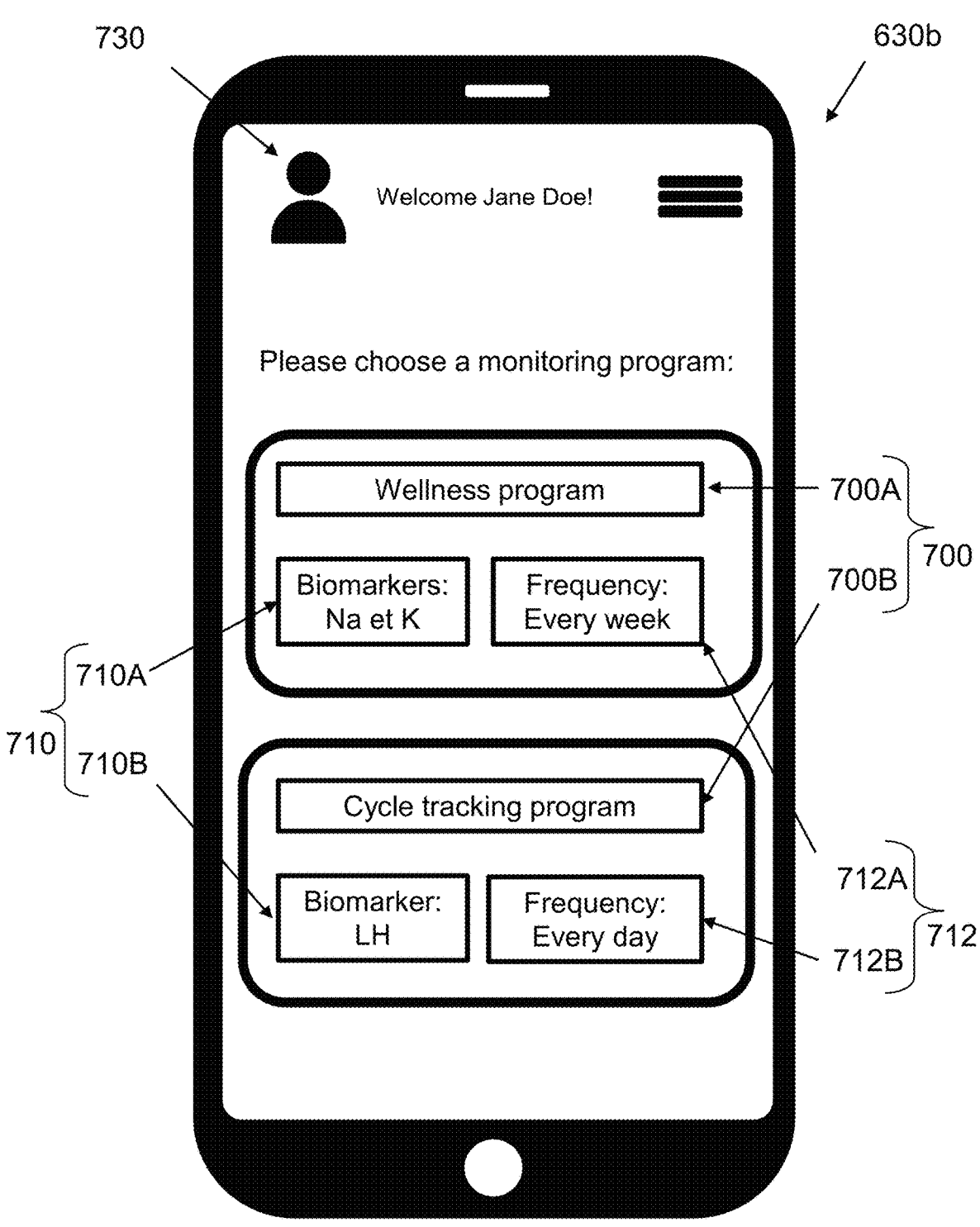
FIG. 7 illustrates a mobile terminal with an example of an app to choose a monitoring program.

A monitoring program 700 includes at least one biomarker 710 to measure, and a measurement frequency 720 associated to each biomarker. The monitoring program 700 may further comprise datum related to an interval of the day to beneficially analyze the biomarker (for example in the morning for LH or in the afternoon for pH). As illustrated on FIG. 7, the monitoring program is for example a "wellness program" 700A associated to biomarkers 710A to be tested with a measurement frequency 720A (e.g., each week in the illustrated example or after each effort), such as sodium, potassium, vitamins, protein, etc (e.g., sodium and potassium in the illustrated example). As another example, the monitoring program may be a "cycle tracking program" 700B associated to biomarkers 710B related to woman health as LH in the illustrated example and/or hCG, etc to be tested with a measurement frequency 720B (e.g., each day as in the illustrated example). The selected monitoring program is sent by the mobile terminal 630*b* to the server 630*a*. The measurement plan(s) are generated by the server 320*a* using the selected monitoring program and the user profile 730. If the monitoring program comprises at least two biomarkers to analyze, a measurement plan is generated for each biomarker. For example, if the user selects a "wellness program", the server generates a measurement plan associated to sodium and another measurement plan associated to potassium, with temporal analyzing windows adapted to the lifestyle habits of the user indicated in the user profile 730 (which includes "Jane Doe" as user characteristics "identity of the user") and optionally adapted to the beneficial interval of the day to analyze the biomarker. The server 630*a* is then configured to send the generated measurement plan(s) to the urine analysis device 100. Alternatively, the measurement plan is generated by the mobile terminal 630*b* and may be sent afterward to the server 630*a*.

In an example, a user may select a monitoring program 700 among the plurality of available programs. After this selection, the user may be invited to choose the temporal analyzing windows that fit him or her most. As the user is identified on the app by his or her user profile 730, the server 630*b* generates a measurement program associated to this user profile and the measurement program includes the temporal analyzing windows that were chosen by the user. In another example, when the user profile includes awakening habits, the server 630*b* generates a measurement program associated to the user profile and the temporal analyzing windows may be selected automatically based on the awakening habits of the user profile. A confirmation may be sent to the user.

In an embodiment, the mobile terminal 630*b* is configured to receive a reminder notification, sent by the server 630*a*, before or at the beginning of a temporal analyzing window. In that way, the user is reminded to go urinate in the toilets during the temporal analyzing window so that an analyze of his or her urine is performed.

In an embodiment, the urine analysis device 100 is configured to send the measurement data to a remote system 630, notably to the server 630*a*. The remote server 630 is configured to associate the measurement data to the user profile associated to the ongoing temporal analyzing window. This enables a user discrimination, even if no identification is carried out. Indeed, as each temporal analyzing window is associated to a specific registered user, so that the measurement data of a user urinating in this temporal analyzing window is associated to the user profile of the specific registered user.

In an embodiment, the mobile terminal 630*b* is configured to receive a confirmation request, send by the server 630*a*. The confirmation request includes a request for input from the user to confirm that the measurement data are to be associated to his or her user profile. In an embodiment, the confirmation request may comprise a transfer request to associate the measurement data to another registered user. In particular, when the user associated to the ongoing temporal analyzing window declines the measurement data to be associated to his or her user profile because he or she was not the urinating user (e.g., by using the app connected to his or her user profile on his or her mobile terminal), the user associated to the ongoing temporal analyzing window may select in the mobile terminal 630*b*, notably in the app, another registered user profile to be associated with the measurement data. Following the transfer request, the measurement data may be associated to the selected user profile, or an additional confirmation request may be sent to the mobile terminal 630*b* of the selected user (e.g., to the app connected to the user profile that was selected). The additional confirmation request includes a request for input from the selected user to confirm that the measurement data are to be associated to his or her user profile.

When a temporal analyzing window is ongoing, (i.e. the actual internal time value of the internal clock 618 is within the active analyzing window), the ongoing analyzing window is closed after measurement data is associated to the user profile associated with the ongoing analyzing window.

In an embodiment, the user may modify his or her user profile using an external device 630, notably the terminal mobile 630*b*. The terminal mobile 630*b* is configured to send and synchronize the modified user profile with the server 630*a*. In response, the server 630*a* is configured to update the at least one measurement plan, using the modified user profile. The server 630*a* is then configured to send to the urine analysis device 100 the at least one updated measurement plan, in replacement of the at least one ongoing measurement plan. In an embodiment, the server 630*a* is configured to synchronize once a day with the urine analysis device 100, for example at midnight. The fewer the number of synchronizations, the longer the battery 640 lasts.

In an embodiment, a temporal analyzing window is classified as unconclusive when no urine sample has been analyzed during the temporal analyzing window. The external device 630, notably the server 630*a*, may be configured to count the number of temporal analyzing windows classified as unconclusive over a predetermined period of time, for example over a week. If the number of temporal analyzing windows classified as unconclusive over the predetermined period of time is greater than a predetermined threshold, for example two or three, the server 630*a* is configured to send to the terminal mobile 630*b* a notification asking for a user input to modify the upcoming temporal analyzing windows of the measurement plan. For example, after a user wakes up several times in the week later than indicated in his or her user profile and misses several temporal analyzing windows in the week, the user may receive a notification on his or her terminal mobile 630*b* (e.g., in the app) inviting him or her to modify his or her awakening habits in his or her user profile.

Method of Monitoring at Least a Biomarker

Figure 8:
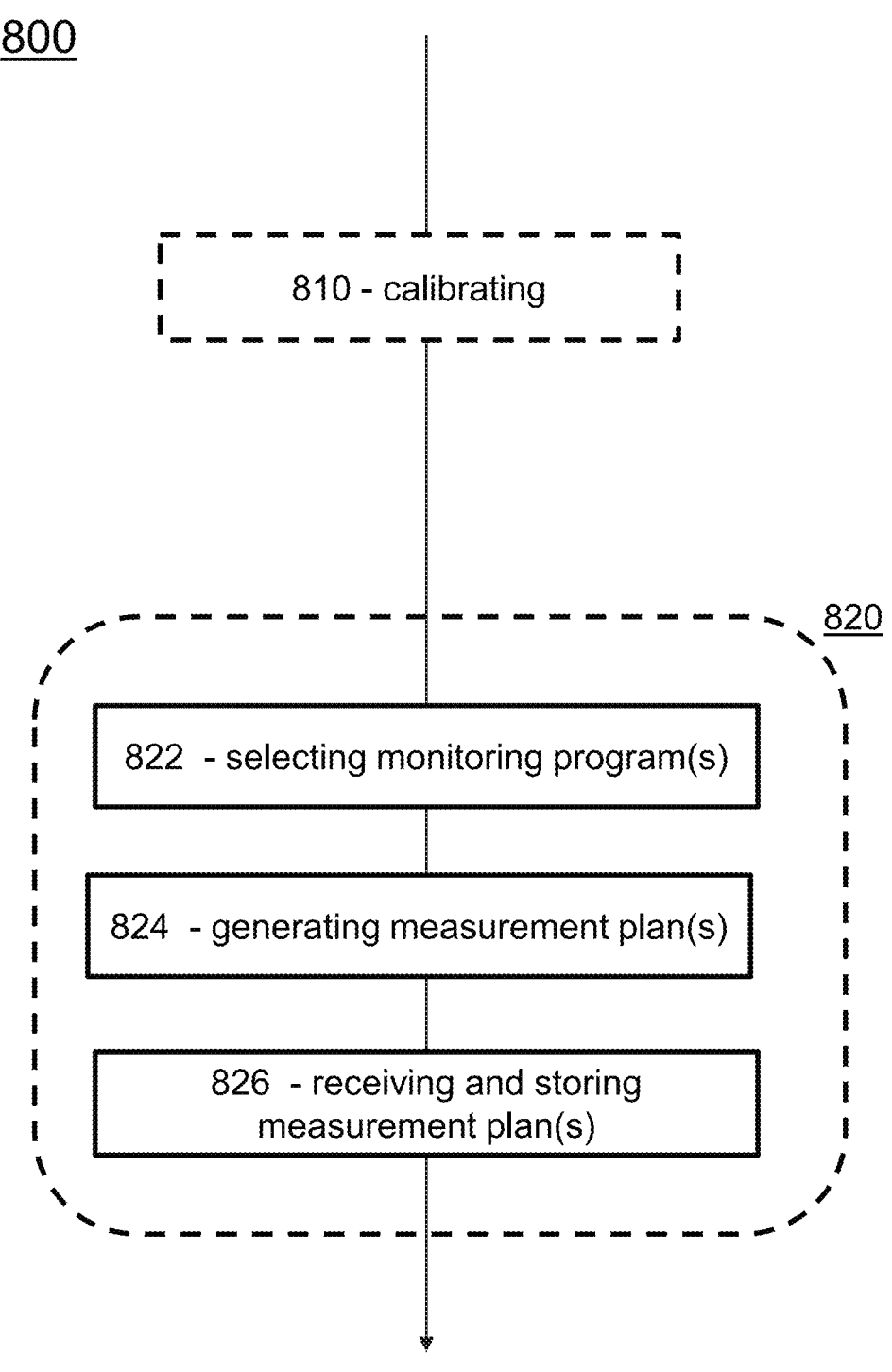
FIG. 8 shows a schematical view of measurement plans associated to different registered user of the urine analysis device.

A method of monitoring 800 at least one biomarker of a registered user with the urine analysis device 100 will now be described, in reference to FIGS. 8 and 9.

Figure 10:
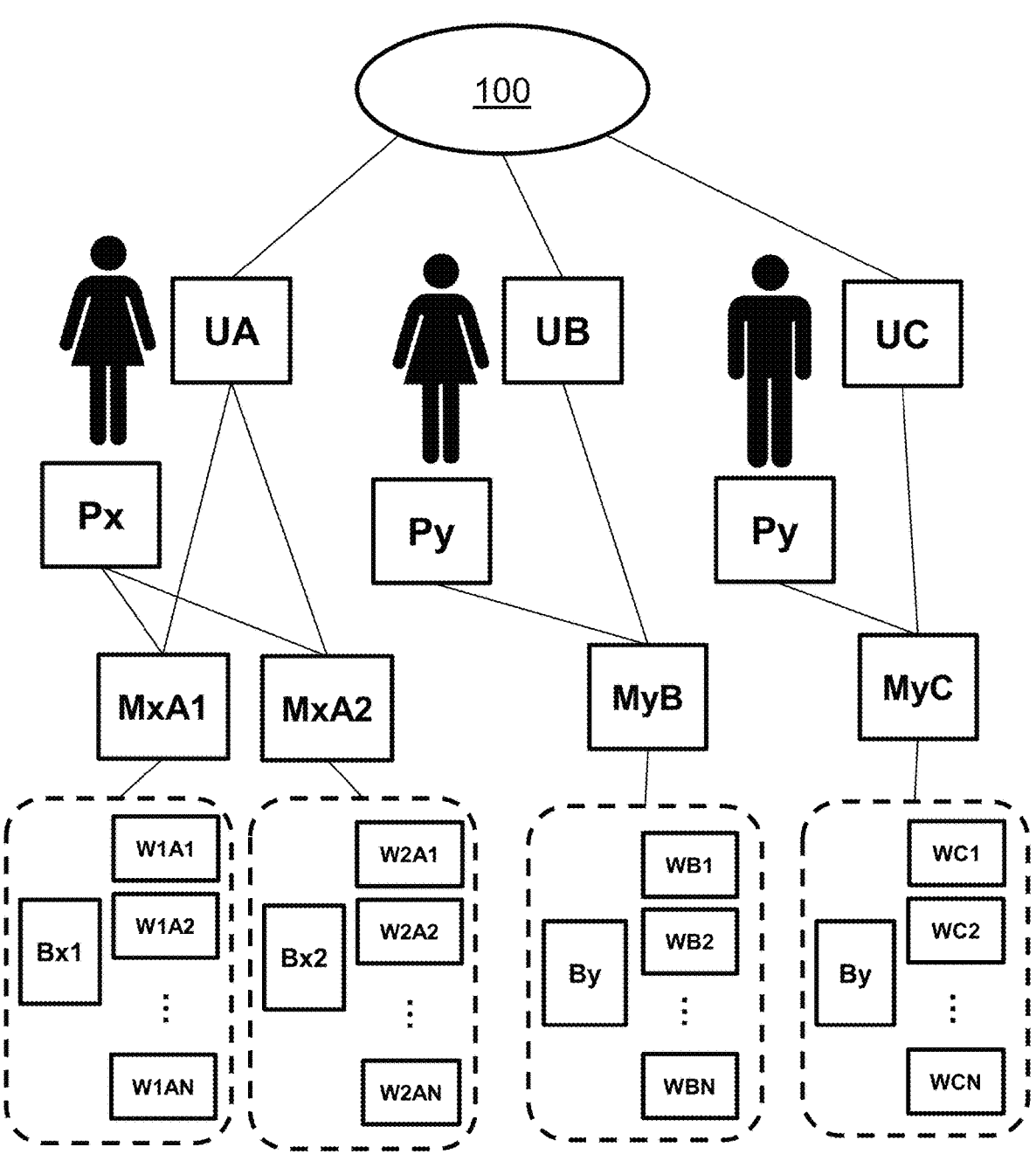
FIG. 10 illustrates a flowchart of monitoring at least one biomarker following the flowchart of FIG. 9.

Referring to FIG. 10, the method will be illustrated with a non-limiting example in which three registered users, that is to say three users with a corresponding user profile registered in the memory 614 of the urine analysis device 100. However, the method may be applied to any number of registered users. In the example, the three users: a first woman A, a second woman B and a man C. Each of the user A, B, C is associated with a user profile, referenced respectively UA, UB and UC. Each registered user may have completed his or her user profile in a his or her respective terminal mobile 630b and each user profile is synchronized at least partially with the server 630a and the urine analysis device 100.

The method of monitoring 800 may comprise an optional calibration phase 810, a measurement plan configuration phase 820, a collecting/analyzing phase 910, an attribution phase 920 and a modification phase 930. Each phase may be carried out independently from the other phases. In particular, phases 910 and 920 may be carried out several times in a row.

In an embodiment in which an identification is carried out, the method may comprise the calibration phase 810 comprising calibrating the urine analysis device 100 for each registered user, and more particularly calibrating the identification system 310. During this phase 810, the radar sensor sends a radar signal in direction of a urine stream of a calibration urination of the registered user and receives a reflected radar signal. The urine analysis device 100 determines a user radar pattern associated to the user profile of the registered user based on the reflected radar signal. The calibration phase 810 may be performed before, in parallel or after the measurement plan configuration phase 820.

In the example, users A, B and C are invited, for example by a notification received on their terminal mobile 630b, to each go to the toilets 102 and to have at least a calibration urination on the urine analysis device 100. The urine analysis device 100 determines then a user radar pattern for each user.

In a variant, in an embodiment with identification, no calibration is carried out. For example, the radar patterns associated to each registered user may be already stored in the urine analysis device 100 (or even no calibration is needed for the identification system).

In another variant, no identification is carried out during the method 800 and as a consequence no calibration is carried out.

The method further comprises the measurement plan configuration phase 820. Phase 820 comprises selecting 822 a monitoring program, in which at least one registered user A, B, C selects on a user external device 630 a monitoring program among a plurality of predetermined monitoring programs, as illustrated on FIG. 7.

In the example, user A selects monitoring program noted Px and users B and C selects the same monitoring program noted Py.

The monitoring program includes at least a biomarker to measure and a measurement frequency associated to each biomarker (e.g., twice a day, every day, twice a week, every week, every two weeks, every month, etc.).

In the example, monitoring program Px is associated to two biomarkers Bx1 (e.g., Sodium) and Bx2 (e.g., Potassium). Bx1 is associated to a daily measure frequency and Bx2 is associated to a weekly measure frequency. Monitoring program Py is associated to a single biomarker By (e.g. pH) with a daily measure frequency.

Then, the phase 820 comprises generating 824 at least one measurement plan using the selected monitoring program and the user profile. When the monitoring program comprises at least two biomarkers to analyze, a measurement plan is generated for each biomarker.

In the example, based on the user profile UA and the monitoring program Px, two monitoring programs MxA1 and MxA2 are generated. MxA1 comprises a datum related to biomarker Bx1 to analyze and a schedule of temporal analyzing windows W1A1, W1A2, . . . , WiAN to analyze the biomarker Bx1. MxA2 comprises a datum related to biomarker Bx2 to analyze and a schedule of temporal analyzing windows W2A1, W2A2, . . . , W2AN to analyze the biomarker Bx2.

Based on the user profile UB and the monitoring program Py, one monitoring program MyB is generated. MyB comprises a datum related to biomarker By to analyze and a schedule of temporal analyzing windows WB1, WB2, . . . , WBN to analyze the biomarker By.

Based on the user profile UC and the monitoring program Py, one monitoring program MyC is generated. MyC comprises a datum related to biomarker By to analyze and a schedule of temporal analyzing windows WC1, WC2, . . . , WCN to analyze the biomarker By.

The temporal analyzing windows may be generated based on lifestyle habits, notably based on awakening habits and/or home presence habits for example.

For example, user A wakes up usually around 8 am during the week, excepted on Wednesday where she works on remote and wakes up around 9 am. During the weekend, she wakes up around 9:30 am to 10:30 am. As a consequence, as illustrated on FIG. 11, the temporal analyzing windows are defined around these usual wakeup time. It can be noted that on Monday, the temporal analyzing windows for the two measurements plan are completely overlapping. It can be also noted that the temporal analyzing windows last longer during the weekend than during the rest of the week.

In a similar way, user B wakes up earlier so that the temporal analyzing windows for user B are defined earlier than for user A. However, it can be noted that some temporal analyzing windows of measurement plans for user A and for user B are partially overlapping.

User C has indicated in his user profile that he usually does not urinate in the morning during the week but rather when coming back from work, but he urinates in the morning the weekend. He has further indicated that he comes back usually around 7:30 pm. As a consequence, as illustrated on FIG. 11, the temporal analyzing windows are defined around these usual coming back from work time during the week and around the usual wakeup time during weekend.

Alternatively or complementarily, the temporal analyzing windows are generated with user inputs, or with a combination of the lifestyle habits and user inputs.

Then, the phase 820 comprises receiving and storing 826, by the urine analysis device 100, the at least one measurement plan in the memory 614 of the control circuitry 610.

The method comprises then the collecting/analyzing phase 910. The phase 910 comprises opening 910 at least a temporal analyzing window when an internal time value of the internal clock 618 of the control circuitry 610 matches the starting point of the temporal analyzing window. Opening 910 means, in terms of technical definition, that the urine analysis device 100 is unlocked to perform a measurement.

For example, supposing the current time is 8 am on Monday, analyzing windows W1A1 and W2A1 are opened while WB1 was opened 30 minutes ago.

The external device 630, notably the terminal mobile 630*b* of the registered user associated to the opened temporal analyzing windows (by means of the associated user profile), may receive a reminder notification before, for example 5 minutes before, or at the beginning of the temporal analyzing window.

The phase 910 may comprise activating 914 the urine presence sensor 310 at least in response to determining that an internal time value of the internal clock 618 is within at least one temporal analyzing window. In other words, the urine presence sensor 304 is activated only when at least one temporal analyzing window is opened. Alternatively, the urine presence sensor 310 is always activated.

Then, a user, called hereafter "urinating user", urinates in the toilets 102 and on the urine analysis device 100.

In an embodiment, the phase 910 then comprises identifying 916, by the identification system 310 of the urine analysis device 100, at least a user profile associated with the urinating user. In particular, identifying may comprise comparing the received radar signal of the urinating user to the different user radar patterns of the user profiles stored in the memory 614 of the urine analysis device 100 Those radar patterns were obtained at calibration 810. Identifying may include partially identifying the user by determining on the urinating user at least a user characteristic of the user profile, for example the biological sex of the user.

For example, if the urinating user is user A, who is a female, the identification system 310 identifies that the biological sex of the urinating user is a female. In an embodiment, the identification system 310 may identify the identity of the urinating user, here user A. In other words, the identification system 310 may select a single user profile corresponding to the urinating user, instead of a plurality of user profiles compatible with the urinating user (e.g., selecting all the user profile that includes "woman" as the biological sex in the user profile when the urinating user is a woman).

In a variant, no identification is performed by the urine analysis device 100.

Then, in response to determining that an internal time value of the internal clock 618 is within at least one temporal analyzing window, the phase 910 comprises at least one of collecting 918, by the urine analysis device 100, a urine sample from a urine stream of a urinating user, and analyzing 919, by the urine analysis device 100, the urine sample to obtain measurement data relative to the biomarker associated with the temporal analyzing window.

For example, if a user urinates outside any temporal analyzing window, the urine presence sensor 304 is deactivated and collecting 816 and analyzing 818 is not performed.

In an embodiment, when no identification is performed, at least one of collecting 918 and analyzing 919 the urine sample are carried out only by determining that an internal time value of the internal clock 618 is within at least one temporal analyzing window.

Figure 11:
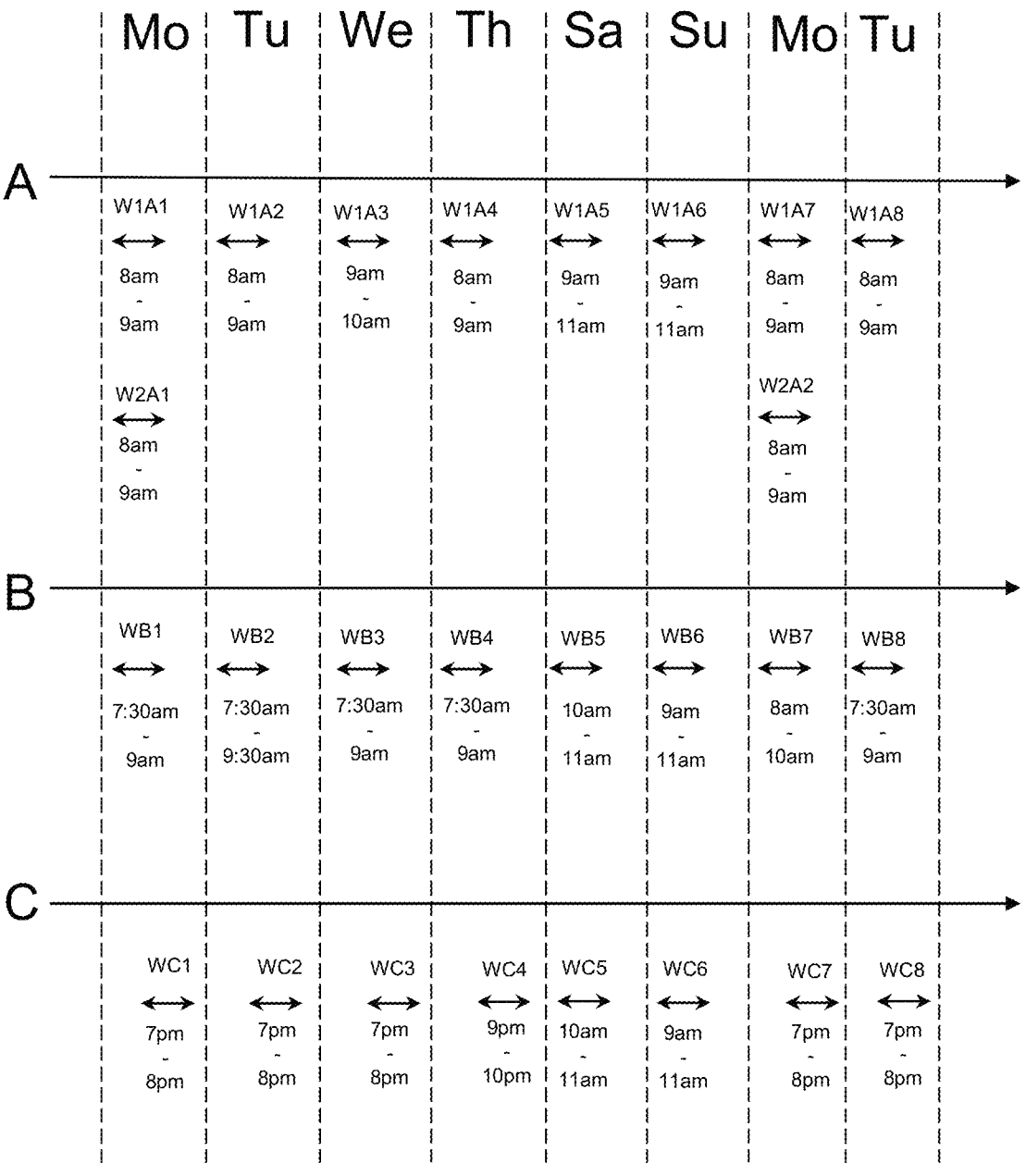
FIG. 11 illustrates a timeline where temporal analyzing windows associated to different user are represented.

For example, assuming urinating user is user C and current time is 7:45 am of Monday. Referring to FIG. 11, temporal analyzing window WB1 is open. As an analyzing window is open, the control circuitry 610 launches collecting 918 and analyzing 919 a urine sample of the urinating user to measure biomarker By.

In an embodiment, at least one of collecting 918 and analyzing 919 the urine sample are carried out in response to further identifying, or in other words discriminating, the urinating user using the at least one user characteristic and the user profile corresponding to the temporal analyzing window.

For example, assuming urinating user is user C and current time is 7:45 am of Monday. Referring to FIG. 11, only temporal analyzing window WB1 is open. Temporal analyzing window WB1 is associated with the measurement plan MyB of user profile UB, whose user characteristic "biological sex of the user" is "female". Now, assuming that the identification system 310 identifies that the urinating user is a male. As the biological sex of the urinating user does not match the user characteristic "biological sex of the user" of the user profile associated to the opened temporal analyzing window, the control circuitry 610 does not launch collecting 918 and analyzing 919 a urine sample of the urinating user.

In another example, assuming urinating user is user A and current time is 7:45 am of Monday. Referring to FIG. 11, only temporal analyzing window WB1 is open. Temporal analyzing window WB1 is associated with the measurement plan MyB of user profile UB, whose user characteristic "biological sex of the user" is "female". Now, assuming that the identification system 310 identifies that the urinating user is a female: as the biological sex of the urinating user matches the user characteristic "biological sex of the user" of the user profile associated to the opened temporal analyzing window, the control circuitry 610 launches collecting 918 and analyzing 919 a urine sample of the urinating user for measuring biomarker By, even if the opened temporal analyzing window is associated to user B. In a variant, if the identification system 310 identifies that the identity of the urinating user as being user A, as the identity of the urinating user does not match the identity of the user profile associated to the open temporal analyzing window, the control circuitry 610 does not launch collecting 918 and analyzing 919 a urine sample of the urinating user. In a variant, if the identification system 310 identifies that the urinating user is user B, then the control circuitry 610 launches collection 918 and analyzing 919.

In another example, assuming urinating user is user A and current time is 8:30 am on Monday. Referring to FIG. 11, temporal analyzing windows W1A1 (corresponding to measurement plan Mx1A, user profile UA, user characteristics "biological sex of the user" is a female, biomarker Bx1), W2A1 (corresponding to measurement plan Mx2A, user profile UA, user characteristics "biological sex of the user" is a female, biomarker Bx2) and WB1 (corresponding to measurement plan MyB, user profile UB, user characteristics "biological sex of the user" is a female, biomarker By) are open. Now, assuming that the identification system 310 identifies that the urinating user is a female: as the biological sex of the urinating user matches user characteristic "the biological sex of the user" of the user profile associated to each of the open temporal analyzing windows, the control circuitry 610 launches collecting 918 and analyzing 919 a urine sample of the urinating user, for measuring biomarkers Bx1, Bx2 and By. In particular, collecting 918 is performed only once to collect a urine sample and analyzing 919 is performed three times in a row, once for each biomarker to analyze. In a variant, assuming the identification system 310 identifies that the identity of the urinating user as being user A, as the identity of the urinating user match the identity of the user profile associated to temporal analyzing windows W1A1 and W2A1, the control circuitry 610 launches collecting 918 and analyzing 919 a urine sample of the urinating user for measuring biomarkers for measuring biomarkers Bx1 and Bx2, but not for measuring By This allows to save a test strip.

Then, the method comprises the attribution phase 920. The phase 920 comprises sending 922, by the urine analysis device 100, the measurement data to a remote system 630, notably to the server 630*a*.

During 924, the measurement data is associated to the user profile corresponding to the ongoing temporal analyzing window. Steps 922 and 924 may be inverted, notably if the urine analysis device 100 is capable of identifying a single user profile for the urinating user.

In an embodiment, the phase 920 comprises receiving 926 by a user external device 630, notably by the mobile terminal 630*b*, a confirmation request including a request for input from the user to confirm that the measurement data is to be associated to his or her user profile. If the user validates the association, the measurement data is definitively associated to the user profile. If the user refuses the association, the measurement data is removed from the user profile. The request may be sent each time measurement data is associated to the user profile or may be sent, in an embodiment, in response to determining that the identification confidence score is lower than a predetermined threshold.

For example, assuming urinating user is user C and current time is 7:45 am of Monday. Referring to FIG. 11, temporal analyzing window WB1 is open. As a temporal analyzing window is open, the control circuitry 610 launches collecting 918 and analyzing 919 a urine sample of the urinating user to measure biomarker By. The measurement data is associated to the user profile UB and a confirmation request is sent to user B who declines that the measurement data is to be associated to his user profile UB. User B may request (for example from the app connected to his or her profile UB on the mobile terminal) a transfer of the measure associated to biomarker By to user profile UC. User C then receives a confirmation request (for example on the app connected to his or her user profile UA) and may validate that the measure associated to biomarker By is to be associated to his user profile UC.

As another example, assuming urinating user is user C and current time is 7:30 pm of Monday. Referring to FIG. 11, temporal analyzing windows WB1 (corresponding to measurement plan MyB, user profile UB, user characteristics "biological sex of the user" is a female, biomarker By), and WC1 (corresponding to measurement plan MyC, user profile UC, user characteristics "biological sex of the user" is a male, biomarker Byy), are opened. Now assuming the identification system 310 has identified the urinating user is a male with 60% confidence score. The control circuitry 610 launches collecting 918 and analyzing 919 a urine sample of the urinating user for measuring biomarker By of the open temporal analyzing window. The measurement data is associated to the user profile UC and a confirmation request is sent to user C who validates that the measurement data is to be associated to his user profile UC.

As another example, assuming urinating user is user A and current time is 8:30 am on Monday. Referring to FIG. 11, temporal analyzing windows W1A1 (corresponding to measurement plan MxA1, user profile UA, user characteristics "biological sex of the user" is a female, biomarker Bx1), W2A1 (corresponding to measurement plan MxA2, user profile UA, user characteristics "biological sex of the user" is a female, biomarker Bx2), WB1 (corresponding to measurement plan MyB, user profile UB, user characteristics "biological sex of the user" is a female, biomarker By), and WC1 (corresponding to measurement plan MyC, user profile UC, user characteristics "biological sex of the user" is a male, biomarker By), are opened. Now, assuming the identification system 310 identifies that the urinating user is a female and the control circuitry 610 launches collecting 918 and analyzing 919 a urine sample of the urinating user, for measuring biomarkers Bx1, Bx2 and By of the open temporal analyzing window. The measurement data associated to biomarkers Bx1 and Bx2 is associated to the user profile UA and the measurement data associated to biomarkers By is associated to the user profile UB. A confirmation request is sent to user A who validates that the measurement data associated to biomarkers Bx1 and Bx2 is to be associated to his user profile UA. A confirmation request is sent to user B who refuses that the measurement data associated to biomarkers By is to be associated to his user profile UB. User B may request (for example from the app connected to his or her profile UB on the mobile terminal), a transfer of the measure associated to biomarker By to user profile UA. User A then receives a confirmation request (for example on the app connected to his or her user profile UA) and may validate that the measure associated to biomarker By is to be associated to his user profile UA.

Then, at 928, the ongoing open temporal analyzing window is closed after that measurement data is associated to the user profile associated with the ongoing temporal analyzing window.

In the previous example, as user A has validated the measurement data associated to biomarkers Bx1 and Bx2, temporal windows W1A1 and W2A1 are closed. On the contrary, as user B has refused the measurement data associated to biomarkers By, temporal window WB1 is still left opened.

In an embodiment, the number of temporal analyzing windows of a same measuring plan classified as unconclusive over a predetermined period of time (for example a week) are counted. If the number of inconclusive temporal analyzing windows is greater than a predetermined threshold (for example 3), the method further comprises: receiving 930, by an external user device, a notification asking the user associated to the measuring plan input to modify notably upcoming temporal analyzing windows of the measurement plan.

For example, if user C comes back from work more around 8 pm than 7:30 pm as indicated in his profile, he may miss too much temporal analyzing windows. He receives then a notification and he modifies his user profile to indicate his updated work schedule. A new measuring plan is then generated and send to the urine analysis device 100.

It will be appreciated that the various embodiments and aspects of the inventions described previously are combinable according to any technically permissible combinations.

The articles "a" and "an" may be employed in connection with various elements and components, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The invention claimed is:

1. A method of monitoring at least one biomarker of a registered user with a urine analysis device in a toilet, the urine analysis device comprising control circuitry, the control circuitry comprising an internal clock and a memory storing at least one measurement plan associated to a user profile of the registered user, the at least one measurement plan including a datum related to a predetermined biomarker to analyze, and at least one temporal analyzing window to analyze the predetermined biomarker, wherein the method comprises:

collecting, by the urine analysis device, a urine sample from a urine stream of a urinating user, and analyzing, by the urine analysis device, the urine sample to obtain measurement data relative to the predetermined biomarker of the urinating user, wherein at least one of collecting and analyzing is performed at least in response to determining that an internal time value of the internal clock is within the at least one temporal analyzing window of the measurement plan.

2. The method according to claim 1, further comprising, before said collecting and/or said analyzing, receiving and storing, by the urine analysis device, the at least one measurement plan in the memory.

3. The method according to claim 1, wherein the measurement data are associated to the user profile corresponding to the temporal analyzing window of the measurement plan.

4. The method according to claim 1, further comprising sending, by the urine analysis device, the measurement data to an external device.

5. The method according to claim 4, further comprising, after said sending, receiving, by the external device, a confirmation request including a request for input from the user to confirm that the measurement data is to be associated to his or her user profile.

6. The method according to claim 1, wherein the memory stores a plurality of measurement plans, wherein at least two windows of two measurement plans are at least partially overlapping.

7. The method according to claim 1, wherein the urine analysis device further comprises a urine presence sensor, wherein said collecting is performed in response to detecting, by the urine presence sensor, urine from a urine stream of the urinating user.

8. The method according to claim 7, further comprising activating the urine presence sensor at least in response to determining that an internal time value of the internal clock is within the at least one temporal analyzing window of the measurement plan.

9. The method according to claim 1, further comprising selecting by the user on an external device a monitoring program among a plurality of predetermined monitoring programs, the monitoring program including at least a biomarker to measure and a measurement frequency associated to each biomarker, wherein the at least one measurement plan is generated using the monitoring program and the user profile.

10. The method according to claim 9, wherein the user profile comprises awakening habits including at least one usual wakeup time for a given day, the at least one temporal analyzing window being generated using the at least one usual wakeup time.

11. The method according to claim 9, wherein the at least one measurement plan is generated further using the associated biomarker to analyze.

12. The method according to claim 1, wherein in response to the user modifying the user profile using an external device, the at least one measurement plan is updated using the modified user profile.

13. The method according to claim 12, further comprising, in response to the at least one measurement plan being updated, receiving, by the urine analysis device at least one regenerated measurement plan once a day, in replacement of at least one ongoing measurement plan.

14. The method according to claim 1, further comprising identifying, by the urine analysis device, at least a user profile associated with the urinating user.

15. The method according to claim 14, wherein said at least one of collecting and analyzing the urine sample is performed in response to determining that one of at least one identified user profile is the user profile corresponding to the temporal analyzing window of the measurement plan.

16. The method according to claim 14, wherein said identifying includes determining at least a user characteristic associated to the urinating user, wherein said at least one of collecting and analyzing the urine sample are carried out in response to further identifying the urinating user using the at least one user characteristic and the user profile corresponding to the temporal analyzing window of the measurement plan.

17. The method according to claim 14, further comprising:

calculating a confidence score related to a probability that the identified user profile is that of the urinating user, and in response to determining that the confidence score is lower than a predetermined threshold, receiving, by an external device of the at least one identified user profile, a confirmation request for input to confirm that the identified user profile is to be associated to the urinating user.

18. The method according to claim 14, wherein said identifying is carried out with a radar sensor arranged in the urine analysis device, wherein the radar sensor sends a radar signal in a direction of the urine stream and receives a reflected radar signal.

19. The method according to claim 1, wherein an analyzing window is classified as inconclusive when no urine sample has been analyzed during the analyzing window, wherein when a number of analyzing windows classified as inconclusive over a predetermined period of time is greater than a predetermined threshold, the method further comprises receiving, by an external device, a notification asking a user input to modify upcoming temporal analyzing windows of the measurement plan.

20. The method according to claim 1, wherein the method further comprises closing an ongoing analyzing window after measurement data is associated to the user profile associated with the ongoing analyzing window.

* * * * *